United States Patent
Bhise et al.

(10) Patent No.: US 11,040,008 B2
(45) Date of Patent: Jun. 22, 2021

(54) PHARMACEUTICAL COMPOSITIONS OF MELOXICAM

(71) Applicant: Slayback Pharma LLC, Princeton, NJ (US)

(72) Inventors: Rahul Dhulaji Bhise, Hyderabad (IN); Ashish Anilrao Dubewar, Hyderabad (IN); Prashanth Reddy Molugu, Hyderabad (IN)

(73) Assignee: Slayback Pharma LLC, Princeton, NJ (US)

( * ) Notice: Subject to any disclaimer, the term of this patent is extended or adjusted under 35 U.S.C. 154(b) by 0 days.

(21) Appl. No.: 16/371,293

(22) Filed: Apr. 1, 2019

(65) Prior Publication Data

US 2019/0307681 A1 Oct. 10, 2019

(30) Foreign Application Priority Data

Apr. 4, 2018 (IN) .............................. 201841012828

(51) Int. Cl.
| | | |
|---|---|---|
| *A61K 9/107* | (2006.01) | |
| *A61K 47/24* | (2006.01) | |
| *A61K 47/26* | (2006.01) | |
| *A61K 47/12* | (2006.01) | |
| *A61K 47/10* | (2017.01) | |
| *A61K 47/02* | (2006.01) | |
| *A61K 47/44* | (2017.01) | |
| *A61K 9/00* | (2006.01) | |
| *A61K 31/5415* | (2006.01) | |
| *A61P 19/02* | (2006.01) | |

(52) U.S. Cl.
CPC .......... *A61K 9/1075* (2013.01); *A61K 9/0019* (2013.01); *A61K 9/107* (2013.01); *A61K 31/5415* (2013.01); *A61K 47/02* (2013.01); *A61K 47/10* (2013.01); *A61K 47/12* (2013.01); *A61K 47/24* (2013.01); *A61K 47/26* (2013.01); *A61K 47/44* (2013.01); *A61P 19/02* (2018.01)

(58) Field of Classification Search
None
See application file for complete search history.

(56) References Cited

U.S. PATENT DOCUMENTS

| | | | |
|---|---|---|---|
| 6,284,269 B1 | 9/2001 | Struengmann et al. | |
| 6,551,619 B1 * | 4/2003 | Penkier ................ | A61K 9/1075 424/400 |
| 8,512,727 B2 | 8/2013 | Cooper et al. | |
| 8,920,820 B2 | 12/2014 | Folger et al. | |
| 9,345,665 B2 | 5/2016 | Ryde et al. | |
| 9,561,229 B2 | 2/2017 | Ottoboni et al. | |
| 9,974,742 B2 | 5/2018 | Ottoboni et al. | |
| 2002/0035107 A1 | 3/2002 | Henke et al. | |
| 2003/0191187 A1* | 10/2003 | Lee ........................ | A61K 9/0019 514/570 |
| 2005/0288280 A1* | 12/2005 | Friton ................. | A61K 31/5415 514/226.5 |
| 2010/0297252 A1* | 11/2010 | Cooper .................. | A61K 9/146 424/501 |
| 2012/0213855 A1 | 8/2012 | Agarwal et al. | |
| 2014/0303245 A1* | 10/2014 | Sprogoe ............... | A61K 31/557 514/469 |
| 2016/0082013 A1* | 3/2016 | Ottoboni ................ | A61K 47/26 514/230.8 |
| 2016/0206622 A1* | 7/2016 | Ottoboni ............ | A61K 31/5377 |
| 2017/0216205 A1* | 8/2017 | Ottoboni ............... | A61K 9/1075 |
| 2018/0133199 A1* | 5/2018 | Dellamary ............. | A61K 47/38 |

FOREIGN PATENT DOCUMENTS

| | | |
|---|---|---|
| KR | 20140039663 A | 4/2014 |
| WO | 2011086194 A1 | 7/2011 |
| WO | 2019/037757 A1 | 2/2019 |

OTHER PUBLICATIONS

Machine English translation for KR10-2014-0039663. (Year: 2014).*
Internet webpage obtained from Wikipeida website: https://en.wikipedia.org/wiki/Lecithin (date unknown).*
Verma et al., Formulation and Characterization of Meloxicam Loaded Microemulsion for the Treatment of Rheumatoid Arthritis, World Journal of Pharmaceutical Research, vol. 3, Issue 3, 2014, 4305-4335.
Yener et al., Effect of Vehicles on Release of Meloxicam from Various Topical Formulations, The Open Drug Delivery Journal, 2009, 3, 19-23.
International Search Report dated Jun. 25, 2019, for corresponding International Patent Application No. PCT/US2019/025293.
Written Opinion dated Jun. 25, 2019, for corresponding International Patent Application No. PCT/US2019/025293.

* cited by examiner

*Primary Examiner* — Sin J Lee
(74) *Attorney, Agent, or Firm* — Pergament & Cepeda LLP; Anila Kethe; Edward D. Pergament

(57) ABSTRACT

The present invention relates to storage stable emulsion formulations of meloxicam or its pharmaceutically acceptable salts, solvates and hydrates thereof suitable for parenteral administration.

12 Claims, No Drawings

PHARMACEUTICAL COMPOSITIONS OF MELOXICAM

CROSS-REFERENCE TO RELATED APPLICATIONS

This application claims foreign priority to Indian Application No. IN, 201841012828 filed on Apr. 4, 2018, which is incorporated herein by reference in its entirety.

FIELD OF THE INVENTION

The present invention relates to stable emulsion formulations of meloxicam or its pharmaceutically acceptable salts, solvates and hydrates thereof suitable for parenteral administration.

BACKGROUND OF THE INVENTION

The present application relates to stable emulsion formulations of meloxicam or its pharmaceutically acceptable salts, solvates and hydrates thereof, suitable for parenteral administration.

Meloxicam, an oxicam derivative, is a member of the enolic acid group of nonsteroidal anti-inflammatory drugs (NSAIDs). It is reported to be a selective inhibitor of cyclo-oxygenase-2 (COX-2) and exerts potent anti-inflammatory, anti-rheumatism and anti-pyretic activity. The chemical name of meloxicam is 4-hydroxy-2-methyl-N-(5-methyl-2-thiazolyl)-2H-1,2-benzothiazine-3-carboxamide-1,1-dioxide and its chemical structure is represented by the following structural Formula (I).

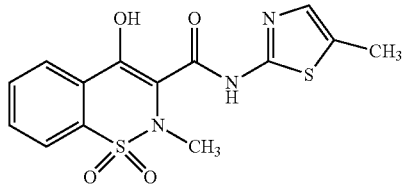

FORMULA (I)

Although meloxicam has been tested and approved only for relief of the signs and symptoms of osteoarthritis, it is also useful in relieving the signs and symptoms of rheumatoid arthritis, lower back pain, and acute pain e.g. treatment of post-surgical pain, treatment of moderate to severe acute postoperative pain, and migraine headaches. Meloxicam may be especially effective for treatment of all types of pain associated with inflammation.

NSAIDs, like meloxicam, are useful in pain management because NSAIDs provide an analgesic effect without the sedation and addictive properties of narcotic analgesics. Furthermore, the long half-life of meloxicam makes it useful for long-lasting relief which is not provided by narcotic analgesics. However, due to their typically long onset of action, conventional NSAIDs, including meloxicam, are frequently inappropriate for management of acute pain.

The form of meloxicam currently marketed in the United States is MOBIC®, provided as 7.5 and 15 mg tablets. The bioavailability of a single 30 mg oral dose is 89% as compared to a 30 mg intravenous bolus injection. The pharmacokinetics of a single intravenous dose of meloxicam is dose-proportional in the range of 5 to 60 mg. After administration of multiple oral doses of meloxicam, the pharmacokinetics is dose-proportional in the range of 7.5 to 15 mg. The rate or extent of absorption is not affected by multiple dose administration. Under fasted steady state conditions, the mean $C_{max}$ is achieved within four to five hours, with a second meloxicam concentration peak occurring at approximately twelve to fourteen hours post-dose, which suggests gastrointestinal recirculation.

Because meloxicam is practically insoluble in water, attaining sufficient bioavailability of this drug is problematic. Prior art methods of increasing the bioavailability of meloxicam include increasing its solubility by forming a cyclodextrin complex of the drug (see U.S. Pat. No. 6,284,269) or by forming a salt of meloxicam with an inorganic or organic base (US Patent Publication No. 2002/0035107 A1).

U.S. Pat. No. 8,512,727 describes pharmaceutical compositions of meloxicam comprising a liquid dispersion medium, particles of meloxicam having an effective average particle size of less than 200 nm; and polyvinylpyrrolidone and sodium deoxycholate as surface stabilizers adsorbed on the surface of the meloxicam particles.

U.S. Pat. No. 9,345,665 describes a method of reducing flake-like aggregates in an injectable nanoparticulate meloxicam composition, comprising: (a) preparing a dispersion of a nanoparticulate active agent and at least one surface stabilizer; and (b) adding a flake-like aggregation reducing agent to the dispersion of step (a), wherein the flake-like aggregation reducing agent is a buffer or a sugar or polyol.

Liquid formulations containing meloxicam are very challenging to make as meloxicam is a molecule having poor solubility characteristics. One means of addressing this challenge is to prepare an emulsion which may both allow preparation of an injectable formulation as well as enhance bioavailability of meloxicam once administered.

Emulsion formulations must also be chemically stable. The drug substance may degrade; for example, lipophilic drugs will partition into the oil phase, which will confer some degree of protection, but hydrolytic degradation may still occur at the oil-water interface. Possible chemical degradation within parenteral fat emulsions includes oxidation of unsaturated fatty acid residues present in triglyceride and lecithin, and hydrolysis of phospholipids leading to the formation of free fatty acids (FFA) and lysophospholipids. Such degradants lower pH, which may then promote further degradation.

In the present application, emulsion formulations of meloxicam are prepared and characterized to identify a formulation and process that will allow meloxicam to be incorporated into an emulsion for intravenous injection and remain stable during the shelf life of the formulation.

SUMMARY OF THE INVENTION

In an embodiment, the present invention relates to stable emulsion formulations of meloxicam or a pharmaceutically acceptable salt, solvate, hydrate thereof, and methods for preparing such compositions.

In another embodiment, the present invention provides stable emulsion formulations of meloxicam suitable for parenteral administration.

In another embodiment, the invention provides stable emulsion formulations of meloxicam suitable for intravenous administration.

An aspect of the invention provides a stable emulsion formulation suitable for intravenous administration comprising an oil phase, wherein the oil phase comprises meloxicam, oil, emulsifier and co-emulsifier; and an aqueous phase, wherein the aqueous phase comprises water, pH modifier and osmotic agent.

Another aspect of the invention provides a stable emulsion formulation suitable for intravenous administration comprising an oil phase, wherein the oil phase consists of meloxicam, oil, emulsifier and co-emulsifier; and an aqueous phase, wherein the aqueous phase consists of water, pH modifier and osmotic agent.

In one embodiment, the composition is an oil-in-water emulsion comprising an oil selected from the group consisting of structurally modified or hydrolyzed coconut oil, olive oil, soybean oil, castor oil, peanut oil, sesame oil, safflower oil, triglycerides, octyl and decyl glycerate, ethyl oleate, glyceryl linoleate, ethyl linoleate, glyceryl oleate, cholesteryl oleate, cholesteryl linoleate or a mixture thereof.

In one embodiment, the composition comprises about 5 wt/wt % (weight/weight %) to 15 wt/wt %, 5 wt/wt % to 10 wt/wt %, 8 wt/wt % to 9 wt/wt %, 7 wt/wt % to 10 wt/wt %, preferably 9.5 wt/wt % oil. In another embodiment, the oil is soybean oil.

In one embodiment, the composition comprises about 20 wt/wt % to 50 wt/wt %, 30 wt/wt % to 50 wt/wt %, 35 wt/wt % to 45 wt/wt %, 30 wt/wt % to 45 wt/wt %, 37 wt/wt % to 42 wt/wt %, 38 wt/wt % to 40 wt/wt %, 30 wt/wt %, 31 wt/wt %, 32 wt/wt %, 33 wt/wt %, 34 wt/wt %, 35 wt/wt %, 36 wt/wt %, 37 wt/wt %, 38 wt/wt %, 39 wt/wt %, 40 wt/wt %, 41 wt/wt %, 42 wt/wt %, 43 wt/wt %, 44 wt/wt %, 45 wt/wt %, 46 wt/wt %, 47 wt/wt %, 48 wt/wt %, 49 wt/wt %, 50 wt/wt % of oil expressed as a percentage of the weight of the oil per the sum of weight of oil, emulsifier and pH modifier in a unit of the composition. In another embodiment, the oil is soybean oil.

In one embodiment, the composition comprises about 1 wt/wt % to 25 wt/wt %, 5 wt/wt % to 25 wt/wt %, 12 wt/wt % to 17 wt/wt %, 13 wt/wt % to 16 wt/wt %, 13 wt/wt % to 15 wt/wt %, or 13 wt/wt % to 14 wt/wt % emulsifier. In another embodiment, the composition comprises about 13 wt/wt %, 13.5 wt/wt %, 14 wt/wt %, 14.5 wt/wt %, 15 wt/wt %, 16 wt/wt %, 17 wt/wt %, 18 wt/wt %, 19 wt/wt % or 20 wt/wt % emulsifier. In another embodiment the emulsifier is a lecithin. In another embodiment the lecithin is an egg yolk lecithin.

In one embodiment, the emulsifier is a phospholipid. In another embodiment, the emulsifier is selected from the group consisting of egg phospholipids, soy phospholipids, phosphatidylcholines, phosphatidylethanolamines, phosphatidylserines, phosphatidylglycerols, phosphatidylinositols, phosphatidic acids, mixed chain phospholipids, lysophospholipids, hydrogenated phospholipids, partially hydrogenated phospholipids, and mixtures thereof.

In one embodiment, the composition comprises a co-emulsifier. In another embodiment, the co-emulsifier is ethanol.

In one embodiment, the composition comprises about less than 10 wt/wt %, 1 wt/wt % to 9 wt/wt %, or 2 wt/wt % to 6 wt/wt % co-emulsifier. In another embodiment, the composition comprises less than 10 wt/wt %, less than 9 wt/wt %, less than 8 wt/wt %, less than 7 wt/wt %, less than 6 wt/wt %, less than 5 wt/wt %, less than 4 wt/wt %, less than 3 wt/wt %, less than 2 wt/wt % or less than 1 wt/wt % co-emulsifier. In an embodiment, the composition comprises 3 wt/wt % of co-emulsifier.

In one embodiment, the composition comprises about less than 10 wt/wt %, 1 wt/wt % to 9 wt/wt %, or 3 wt/wt % to 6 wt/wt % ethanol. In another embodiment, the composition comprises less than 10 wt/wt %, less than 9 wt/wt %, less than 8 wt/wt %, less than 7 wt/wt %, less than 6 wt/wt %, less than 5 wt/wt %, less than 4 wt/wt %, less than 3 wt/wt %, less than 2 wt/wt % or less than 1 wt/wt % ethanol.

In one embodiment, the composition comprises 13 wt/wt % to 20 wt/wt % emulsifier 7 wt/wt % to 10 wt/wt % oil and 1 wt/wt % to 10 wt/wt % co-emulsifier.

In a further embodiment, the composition comprises 13 wt/wt % to 15 wt/wt % emulsifier 7 wt/wt % to 10 wt/wt % oil and 2 wt/wt % to 4 wt/wt % co-emulsifier.

In one embodiment, the composition comprises egg lecithin, soybean oil and ethanol. In another embodiment, the composition comprises egg lecithin, soybean oil, sucrose, sodium oleate and ethanol. In yet another embodiment, the composition comprises egg lecithin, soybean oil, sodium chloride, sodium oleate and ethanol.

In one embodiment, the composition consists of egg lecithin, soybean oil and ethanol. In another embodiment, the composition consists of egg lecithin, soybean oil, sucrose, sodium oleate and ethanol. In yet another embodiment, the composition consists of egg lecithin, soybean oil, sodium chloride, sodium oleate and ethanol.

In one embodiment, the oil is selected from the group consisting of structurally modified or hydrolyzed coconut oil, olive oil, soybean oil, castor oil, peanut oil and sesame oil.

In one embodiment, the composition comprises 13 wt/wt % to 20 wt/wt % egg lecithin, 7 wt/wt % to 10 wt/wt % soybean oil and 1 wt/wt % to 10 wt/wt % ethanol. In another embodiment, the composition consists of 13 wt/wt % to 20 wt/wt % egg lecithin, 7 wt/wt % to 10 wt/wt % soybean oil and 1 wt/wt % to 10 wt/wt % ethanol.

In an embodiment, the emulsion comprises an aqueous phase which comprises an osmotic agent, a pH modifier, and water.

In one embodiment, the composition comprises about less than 30 wt/wt %, 2 wt/wt % to 20 wt/wt %, 3 wt/wt % to 15 wt/wt %, or 3 wt/wt % to 8 wt/wt % osmotic agent. In another embodiment, the composition comprises about 0.5 wt/wt % 1 wt/wt %, 2 wt/wt %, 3 wt/wt %, 4 wt/wt %, 5 wt/wt %, 6 wt/wt %, 7 wt/wt %, 8 wt/wt %, 9 wt/wt %, or 10 wt/wt %, 11 wt/wt %, 12 wt/wt %, 13 wt/wt %, 14 wt/wt %, 15 wt/wt %, 16 wt/wt %, 17 wt/wt %, 18 wt/wt %, 19 wt/wt %, or 20 wt/wt %, 21 wt/wt %, 22 wt/wt %, 23 wt/wt %, 24 wt/wt %, 25 wt/wt % osmotic agent. In still another embodiment, the composition comprises no osmotic agent.

In one embodiment, the composition comprises 13 wt/wt % to 20 wt/wt % emulsifier 7 wt/wt % to 10 wt/wt % oil, 1 wt/wt % to 10 wt/wt % co-emulsifier and 3 wt/wt % to 8 wt/wt % osmotic agent. In a further embodiment, the composition comprises 13 wt/wt % to 15 wt/wt % emulsifier 7 wt/wt % to 10 wt/wt % oil, 2 wt/wt % to 4 wt/wt % co-emulsifier and 5 wt/wt % to 7 wt/wt % osmotic agent. In one embodiment, the composition comprises 13 wt/wt % to 20 wt/wt % egg lecithin, 7 wt/wt % to 10 wt/wt % soybean oil, 1 wt/wt % to 10 wt/wt % ethanol and 3 wt/wt % to 8 wt/wt % sucrose.

In one embodiment, the composition consists of 13 wt/wt % to 20 wt/wt % emulsifier 7 wt/wt % to 10 wt/wt % oil, 1 wt/wt % to 10 wt/wt % co-emulsifier and 3 wt/wt % to 8 wt/wt % osmotic agent. In a further embodiment, the composition consists of 13 wt/wt % to 15 wt/wt % emulsifier, 7 wt/wt % to 10 wt/wt % oil, 2 wt/wt % to 4 wt/wt % co-emulsifier and 5 wt/wt % to 7 wt/wt % osmotic agent. In one embodiment, the composition consists of 13 wt/wt % to 20 wt/wt % egg lecithin, 7 wt/wt % to 10 wt/wt % soybean oil, 1 wt/wt % to 10 wt/wt % ethanol and 3 wt/wt % to 8 wt/wt % sucrose.

In one embodiment, the osmotic agent is selected from a group consisting of glycerol, sorbitol, xylitol, mannitol, glucose, trehalose, maltose, sucrose, raffinose, lactose, dextran, polyethylene glycol, or propylene glycol. In another embodiment, the osmotic agent is an inorganic salt such as sodium chloride and mixtures thereof.

In one embodiment, the pH modifier is selected from a group consisting of sodium hydroxide, potassium hydroxide, magnesium hydroxide, sodium carbonate, Tris, sodium linoleate, sodium oleate, oleic acid, potassium carbonate, potassium linoleate, potassium oleate, and mixtures thereof.

In one embodiment, the composition has a pH of about 5 to 10, 6 to 9, 7 to 9, 7.5 to 9, 7.5 to 8.5, 8 to 9, 6 to 8, 7 to 8, or 6, 7, 8, 9 or 10.

In one embodiment, the composition is a stable system maintaining an intensity-weighted mean droplet particle size as determined by dynamic light scattering (DLS) or static light scattering (SLS) of about 50 nm to 1000 nm, 50 to 500 nm, 50 nm to 400 nm, 50 nm to 300 nm, 50 nm to 200 nm or 50 nm to 100 nm. In another embodiment, the average droplet size is maintained below 500 nm for a period of at least 1 month, 3 months, 6 months, 9 months, 12 months, 2 years or 3 years at room temperature. In another embodiment, the average droplet size is maintained below 500 nm for a period of at least 1 month, 3 months, 6 months, 9 months, 12 months, 2 years or 3 years at 5° C.

In another aspect, a method for preparing an emulsion comprising meloxicam for parenteral administration is provided. In one embodiment, the administration is intravenous administration.

In one embodiment, the method comprises: a) preparing an oil phase by dissolving meloxicam and an emulsifier in ethanol; adding the said ethanol solution to oil to generate an oil-based mixture; b) preparing an aqueous phase by mixing water with an osmotic agent and a pH modifier to generate an aqueous mixture; c) combining the oil-based mixture and the aqueous mixture and subjecting the combined mixtures to high speed homogenization to generate a crude emulsion; and d) subjecting the crude emulsion to high pressure homogenization to generate a fine emulsion.

In another embodiment, the method comprises: a) preparing an oil phase by dissolving meloxicam in ethanol and oil, adding emulsifier to the said ethanol solution in order to generate an oil-based mixture; b) preparing an aqueous phase by mixing water, with a osmotic agent, and with a pH modifier to generate an aqueous mixture; c) combining the oil-based mixture and the aqueous mixture and subjecting the combined mixtures to high speed homogenization to generate a crude emulsion; and d) subjecting the crude emulsion to high pressure homogenization to generate a fine emulsion.

In one embodiment, the dissolution in ethanol is performed at a temperature of about 25° C. to 80° C., 40° C. to 75° C., 60° C. to 70° C. or at about 25° C., 35° C., 45° C., 60° C., 65° C., 70° C. or 75° C.

In one embodiment, the high-speed homogenization is performed at a speed of about 2,000 rpm (revolutions per minute) to 25,000 rpm. In another embodiment, the high-speed homogenization is performed at a speed of about 20,000 rpm. In yet another embodiment, the high-speed homogenization is performed at a speed of about 15,000 rpm.

In one embodiment, the high-speed homogenization is performed for a time period of about 0.5 min to 1 hour, 1 min to 45 min, or 1 min to 30 min. In another embodiment, the high-speed homogenization is performed for a time period of about 20 to 40 min or for about 30 min.

In one embodiment, the high-speed homogenization is performed at about 2° C. to about 60° C., 20° C. to about 60° C., about 30° C. to about 50° C., or about 35° C. to about 45° C. In another embodiment, the high-speed homogenization is performed at about 25° C., 30° C., 35° C., 40° C., 45° C. or 50° C.

In one embodiment, the high-pressure homogenization is performed at a pressure of about 5,000 psi (pounds per square inch) to 30,000 psi. In another embodiment, the high-pressure homogenization is performed at a pressure of about 20,000 psi.

In one embodiment, the high-pressure homogenization is performed with cooling. In another embodiment, the high-pressure homogenization is performed with cooling which is sufficient to bring the temperature of the emulsion at the outlet of the process to about 2° C. to about 60° C., about 10° C. to about 40° C., about 20° C. to about 30° C., or to about 20° C., 25° C. or 30° C. within the time period.

In one embodiment, the method further comprises sterilizing the fine emulsion to generate the final emulsion, wherein the final emulsion is suitable for injection into a subject.

In one embodiment, sterilization of the fine emulsion comprises filtering the fine emulsion through a nylon filter, a PVDF filter or a PES filter. In yet another embodiment, the filter has a pore size of about 0.2 μm.

DETAILED DESCRIPTION OF THE INVENTION

As used in this specification, the singular forms "a," "an," and "the" include plural referents unless the context clearly dictates otherwise. Thus, for example, reference to a "polymer" includes a single polymer as well as two or more of the same or different polymers, reference to an "excipient" includes a single excipient as well as two or more of the same or different excipients, and the like.

Where a range of values is provided, it is intended that each intervening value between the upper and lower limit of that range and any other stated or intervening value in that stated range is encompassed within the disclosure. For example, if a range of 1 micrometre to 8 micrometres is stated, it is intended that 2 micrometres, 3 micrometres, 4 micrometres, 5 micrometres, 6 micrometres, and 7 micrometres are also explicitly disclosed, as well as the range of values greater than or equal to 1 micrometre and the range of values less than or equal to 8 micrometres. As used herein, the term "about" means ±1% or ±5% of the value being modified.

The term "emulsion" or "emulsion formulation" means a colloidal dispersion of two immiscible liquids in the form of droplets, whose diameter, in general, is between 10 nanometres (nm) and 100 micrometres (μm). An emulsion is denoted by the symbol O/W (oil-in-water) if the continuous phase is an aqueous solution and by W/O (water-in-oil) if the continuous phase is an oil. Other examples of emulsions such as O/W/O (oil-in-water-oil) include oil droplets contained within aqueous droplets dispersed in a continuous oil phase.

"Physically stable" emulsions will meet the criteria under USP <729>, which defines universal limits for (1) mean droplet size not exceeding 500 nm or 0.5 μm and (2) the population of large-diameter fat globules, expressed as the volume-weighted percentage of fat greater than 5 μm (PFAT5) not exceeding 0.05%, at 5° C. or room temperature for a designated storage time period. In addition, physically stable emulsions will have no visible meloxicam crystals upon storage at 5° C. or room temperature for a designated time period. Crystals are considered visible when viewed at magnification of 4 times to 10 times. An emulsion is physically stable if it meets the criteria under USP <729> and meloxicam crystals are not visible upon storage at 5° C. or room temperature for a time period equal to or at least 1 week, 2 weeks, 4 weeks, 1 month, 2 months, 6 months, 1 year or 2 years.

"Chemically stable" emulsions of the disclosure are ones in which the concentration of the active component (i.e., the drug being delivered) does not change by more than about 20% under appropriate storage conditions for at least 1 month. In certain embodiments, the meloxicam concentration in an emulsion of the present disclosure does not change by more than about 5%, 10%, 15% or 20% under appropriate storage conditions for at least 1, 2, 3, 4, 5, 6, 9, 12, 15, 18, or 24 months.

In one example, the stable emulsion compositions of the disclosure are stable over a wide range of temperatures, e.g., −20° C. to 40° C. The compositions of the disclosure may be stored at about 5° C. to about 25° C.

The term "oil phase" refers to the non-aqueous portion of oil-in-water emulsion. The term "aqueous phase" refers to the non-oil portion of an oil-in-water emulsion.

An "emulsifier" refers to a compound that deters the separation of the injectable emulsion into individual oil and aqueous phases. Emulsifiers useful in the present disclosure generally are (1) compatible with the other ingredients of the stable emulsions of the present disclosure, (2) do not interfere with the stability or efficacy of the drugs contained in the emulsions, (3) are stable and do not deteriorate in the preparation, and (4) are non-toxic.

The present disclosure is directed to stable pharmaceutical compositions including meloxicam, an emulsifier or mixtures of emulsifiers, a co-emulsifier, an oil, with an aqueous phase. The composition is in the form of an oil-in-water emulsion which remains stable over an extended period of time and which is suitable for dilution and intravenous administration.

The active agent, e.g., meloxicam, is present in the oil phase with an emulsifier, a co-emulsifier and an oil. The oil phase is then combined with an aqueous phase comprising water, an osmotic agent and pH modifying agent to generate a stable emulsion.

Suitable emulsifiers include, but are not limited to, propylene glycol mono- and di-fatty acid esters, polyoxyethylene sorbitan fatty acid esters, polyoxyethylene fatty acid esters, polyoxyethylene-polyoxypropylene co-polymers and block co-polymers, salts of fatty alcohol sulphates, sorbitan fatty acid esters, esters of polyethylene-glycol glycerol ethers, oil and wax-based emulsifiers, glycerol monostearate, glycerine sorbitan fatty acid esters and phospholipids.

A "phospholipid" refers to a triester of glycerol with two fatty acids and one phosphate ion. Exemplary phospholipids useful in the present invention include, but are not limited to, phosphatidyl choline, lecithin (a mixture of choline ester of phosphorylated diacylglyceride), phosphatidylethanolamine, phosphatidylglycerol, phosphatidic acid with about 4 to about 22 carbon atoms, and more generally from about 10 to about 18 carbon atoms and varying degrees of saturation. The phospholipids can have any combination of fatty acid as its fatty acyl side chain, for example, the phospholipids can have a saturated fatty acid such as a decanoic acid, lauric acid, myristic acid, palmitic acid, stearic acid, eicosanoid acid, (a C20 saturated fatty acid); sodium behenic acid, or an unsaturated fatty acid such as myristoleic acid, palmitoleic acid, oleic acid, sodium linoleic acid, alpha linolenic acid, sodium arachidonic acid, eicosapentaenoic acid, and the like. The two fatty acyl residues on the phospholipids may be the same or they may be different fatty acids. The phospholipid component of the drug delivery composition can be either a single phospholipid or a mixture of several phospholipids. The phospholipids should be acceptable for the chosen route of administration.

In one aspect, the phospholipids used as emulsifiers in the present invention are naturally occurring phospholipids from a natural origin. For example, naturally occurring lecithin is a mixture of the diglycerides of stearic, palmitic, and oleic acids, linked to the choline ester of phosphoric acid, commonly called phosphatidylcholine, and can be obtained from a variety of sources such as eggs and soya beans. Soy lecithin and egg lecithin (including hydrogenated versions of these compounds) have been characterized in various compositions and are generally recognized to be safe, have combined emulsification and solubilization properties, and tend to be broken down into innocuous substances more rapidly than most synthetic surfactants.

The term "lecithin" includes a complex mixture of acetone-insoluble phosphatides, of which phosphatidylcholine is a significant component. The term lecithin is also used as a synonym for phosphatidylcholine. Useful lecithins include, but are not limited to, egg yolk-, egg-, soybean-, and corn-derived lecithin. In one embodiment, the emulsifier is lecithin, such as egg yolk-derived lecithin. The terms egg lecithin and egg yolk derived lecithin are used interchangeable throughout. The compositions described herein preferably comprise lecithin as an emulsifier.

"Oil" refers to an organic liquid of mineral, vegetable, animal, essential or synthetic origin, including, for example, aliphatic or wax-based hydrocarbons, aromatic hydrocarbons or mixed aliphatic and aromatic hydrocarbons.

The oil (hydrophobic) phase comprises an oil. Triglycerides are exemplary oils for use in the compositions described herein. In certain embodiments the oil is or comprises a vegetable oil. "Vegetable oil" refers to oil derived from plant seeds or nuts. Vegetable oils are typically "long-chain triglycerides" (LCTs), formed when three fatty acids (usually 14 to 22 carbons in length, with unsaturated bonds in varying numbers and locations, depending on the source of the oil) form ester bonds with the three hydroxyl groups on glycerol. In certain embodiments, vegetable oils of highly purified grade (also called "super refined") are used to ensure safety and stability of the oil-in-water emulsions. In certain embodiments hydrogenated vegetable oils, which are produced by controlled hydrogenation of the vegetable oil, may be used. Exemplary vegetable oils include but are not limited to almond oil, babassu oil, black currant seed oil, borage oil, canola oil, castor oil, coconut oil, corn oil, cottonseed oil, olive oil, peanut oil, palm oil, palm kernel oil, rapeseed oil, safflower oil, soybean oil, sunflower oil and sesame oil. Hydrogenated and/or or partially hydrogenated forms of these oils may also be used. In specific embodiments, the oil is or comprises safflower oil, sesame oil, corn oil, olive oil and/or soybean oil. In more specific embodiments, the oil is or comprises safflower oil, and/or soybean oil.

Meloxicam is first mixed with an emulsifier such as a phospholipid emulsifier. The phospholipid emulsifier is added to a concentration of greater than 1 wt/wt %, but less than 25 wt/wt % of the emulsion.

The mixture of meloxicam and emulsifier is dissolved in a co-emulsifier such as a short chain alcohol (1 to 6 carbons). The co-emulsifier is ethanol. The mixture is mixed at an elevated temperature, such as at about 60° C. or 70° C. or at an elevated temperature within the range of about 50° C. or 70° C., until meloxicam and emulsifier are dissolved. This mixture is then combined with the oil, such as soybean oil, by mixing again at an elevated temperature such as at about 60° C. to produce the oil phase containing meloxicam.

Excess co-emulsifier can be removed by standard evaporation methods including heating, or pressure reduction, or a combination thereof such employed in a rotary evaporator. In this process, about 10% to 100%, 20% to 95%, 80% to 100%, 90% to 100%, or 95% to 100% of the ethanol evaporates depending on preparation scale, any pressure reduction, and heating time.

In one embodiment, the meloxicam and the emulsifier are dissolved in a co-emulsifier and an oil. The co-emulsifier is ethanol, the oil is soybean oil, however, the methods can be used with any one or more of the co-emulsifiers and oils described herein. The mixture is mixed at an elevated temperature, such as at about 60° C. or 70° C. or at an elevated temperature within the range of about 50° C. or 70° C., at least until meloxicam and emulsifier are dissolved to produce the oil phase containing meloxicam. The mixture of meloxicam, emulsifier, co-emulsifier and oil are mixed at the elevated temperature for about 15 min to 120 min, about 15 min to 45 min, about 30 min to 90 min, or for about 15 min, 30 min or 50 min.

The aqueous phase of the meloxicam emulsion can be a mixture of water and an osmotic agent, including those such as sucrose, sodium chloride. Also included in the aqueous phase is a pH-modifying agent. Sodium oleate is used to adjust the pH of the emulsion to about 5 to 10, depending on the desired emulsion formulation. The aqueous phase is produced by mixing water with an osmotic agent and sodium oleate as the pH modifying agent. Other pH modifiers that may be used include but are not limited to sodium hydroxide, potassium hydroxide, magnesium hydroxide, Tris, sodium carbonate and sodium linoleate. The pH modifier used is effective for adjusting the pH of the emulsion to a preferred pH of about 5 to 10, 6 to 9, 7 to 8, or about 6, 7, 8 or 9. The aqueous phase can readily form by mixing at room temperature.

In some embodiments, the aqueous phase contains an osmotic agent such as sodium chloride. The osmotic agent is added to an aqueous phase having about 0% to 30%, 5% to 25% or about 20% of the osmotic agent (wt/wt). Accordingly, preferred embodiments include an emulsion in which the aqueous phase comprises an osmotic agent which imparts greater chemical and/or physical stability as compared to an emulsion wherein the aqueous phase contains less than about 10%, 15% or 20% wt/wt osmotic agent.

The pharmaceutical meloxicam compositions of the present disclosure are sterile oil-in-water emulsions comprising the aqueous and oil phases described above. Also encompassed by the disclosure are methods for preparing stable emulsions comprising meloxicam which are suitable for intravenous administration and which can be prepared according to the conventional manufacturing procedures using aseptic techniques.

The aqueous phase is combined with the oil phase, under high-speed homogenization to produce a coarse emulsion. The combined aqueous and oil phases is homogenized using an IKA Ultra-Turrax T25 dispersing instrument at a speed of 20,000 rpm for 1 min. The speed used in this first homogenization step may vary, for example, from 2000 rpm to 25,000 rpm, or from 15,000 rpm to 22,000 rpm. The time of the homogenization step can also vary, for example, from 0.5 min to 1 hour, or from 1 min to 45 min. This crude emulsion is then homogenized into a fine emulsion by a high-pressure homogenizer, which may be a microfluidizer. The interaction chamber and the cooling coil portions of the microfluidizer are cooled by water, such as by an ice bath. The temperature of the ice bath may be between 0 to 10° C., or 2 to 6° C. The temperature of the emulsion coming out of the high-pressure homogenization may be between 0 to 60° C., 15° C. to 60° C., 20° C. to 40° C., or at about 25° C. The microfluidizer is first primed with water, then the crude emulsion is introduced. The output from the homogenizer is initially run to waste to remove priming water, and priming water and emulsion mixtures, and then collected in a clean vessel when the stream becomes consistent in appearance. The high-pressure homogenizer cycle may be repeated to sufficiently reduce oil droplet size. The pressure used for the homogenization may vary. The pressures may be between 5000 and 30,000 psi. The number of passes through the microfluidizer may vary in order to achieve the desired droplet size. The number of passes may be from about 2 to 20, 2 to 15, 4 to 15, 4 to 12 or 7 to 8.

The pharmaceutical formulation may then be passed through a filter system at room temperature, and/or autoclaved, to achieve sterilization. The filters used to achieve sterilization may be chosen by the skilled artisan and may have a nominal pore size of 0.2 μm. The filter material used may vary. For large scale production the method above may need to be modified. A skilled practitioner could combine these materials in a different order and using different processing equipment to achieve the desired end result.

In one embodiment of the disclosure, the homogenization can be done in repeated cycles to achieve an emulsion in which the oil particle/globule size is less than 500 nm with intermediate cooling of the homogenized product to a temperature less than about 25° C.

The final emulsion comprises an oil portion (oil phase) dispersed in an aqueous portion (aqueous phase). The ratio of components to the meloxicam within the oil phase is an important characteristic of the emulsion which may affect stability of the formulation prepared for injection. As described above, the oil phase comprises meloxicam, an oil and an emulsifier, examples of which are provided herein.

An emulsion is prepared which contains about 5 mg to 60 mg of meloxicam, more preferably from about 5 mg to 15 mg, about 30 mg and about 45 mg of meloxicam. The final meloxicam concentration in the emulsion may range from about 0.1 wt/wt % to 5 wt/wt %, more preferably from about 0.2 wt/wt % to 1.0 wt/wt % or 1.5 wt/wt % to 2.0 wt/wt %.

The composition of the present disclosure gives a product suitable for parenteral use because of low globule size. The composition of the present disclosure is easy to use as the product can be diluted with an agent such as an aqueous solution of sucrose, an aqueous solution of maltose or dextrose 5% injection or normal saline to achieve the required concentration for parenteral administration. The composition of the present disclosure also has a prolonged shelf life and hence is suitable for a readily marketable product.

The compositions of the disclosure are both chemically and physically stable. A physically stable emulsion of the invention is one which can be stored under appropriate conditions for at least 1, 2, 3, 4, 5, 6, 9, 12, 15, 18, 24 or 36 months, without an increase in average droplet size above that allowed as stated in USP <729>. As well, the population of large-diameter fat globules should be within the limits stated in USP <729>.

Droplet size limits defined in USP <729> apply throughout the assigned shelf life, which for a commercial pharmaceutical formulation may extend to 2-3 years or longer. All true emulsions are thermodynamically unstable and may over time undergo a range of processes which tend to increase the droplet size. These include direct droplet coalescence, when two droplets collide and form a single new droplet, and aggregation, in which droplets adhere together to form larger masses. Aggregation may in some cases be a precursor of further coalescence into larger droplets. These processes may result in large aggregates rising to the surface of the container, a phenomenon known as 'creaming', and ultimately to free oil being visible on the emulsion surface, known as 'cracking'.

Droplet size measurements such as those defined in USP <729> can measure the initial increases in size, and hence are predictive of emulsion physical stability at an early time, long before the formulation shows macroscopic visible changes. Accordingly, the emulsions as described herein are stable compositions having an intensity-weighted mean droplet diameter less than about 500 nm, 400 nm, 300 nm, 200 nm or 100 nm.

The oil or particle droplet size, i.e. diameter, according to the present disclosure is measured using either dynamic light scattering (DLS) or static light scattering (SLS) instruments. The emulsion preparations as described herein may further comprise a preservative in quantities that preserve the composition. Suitable preservatives used in some of the embodiments of present disclosure include, but are not limited to, disodium edetate, tocopherol, metacresol, phenol, benzalkonium chloride, methyl, ethyl, propyl or butylparaben, benzyl alcohol, phenylethyl alcohol, benzethonium, chlorobutanol, potassium sorbate or combination thereof.

The emulsions of the present invention can be administered to humans and animals via any conventional means including, but not limited to, orally, rectally, ocularly, parenterally (intravenous, intramuscular, or subcutaneous), intracisternally, pulmonary, intravaginally, intraperitoneally, locally (powders, ointments or drops), or as a buccal or nasal spray.

The emulsion preparations of the present invention may be sterilized. Non-limiting examples of sterilization techniques include filtration through a bacterial-retaining filter, terminal sterilization, incorporation of sterilizing agents, irradiation, and heating.

Sterilization may be accomplished by any of the conventional methods including aseptic filling, irradiation and heat sterilization. Heat sterilization is normally performed using steam, preferably wet steam to allow for the use of pressure as a means of temperature control. The time period for the sterilization must be long enough to meet the sterility requirements required of an injectable product. When steam is used, the period may be from about 5 to 30 minutes at temperatures of about 110° C. to 130° C., or from about 10 to 30 minutes at temperatures of about 110° C. to 130° C., preferably at 120° C. to 125° C. for 15 to 30 minutes. In another embodiment, the sterilization can be at 120° C. for 5 to 15 minutes.

A pharmaceutically inert gas may be bubbled into the emulsion to drive out oxygen, which may be selected from nitrogen or carbon dioxide.

Containers suitable according to the present invention are those known in the art. They include vials, syringes, cartridges, pre-filled syringes, auto-injectors, infusion bags, bottles and ampoule presentations. Containers may be fabricated from glass or from polymeric materials. Suitable containers should be of a size sufficient to hold one or more doses of meloxicam.

The present invention provides for compositions in single-dose and/or multi-dose formulations. In some embodiments, the composition may be contained in vials. In some embodiments, the vials may be made from clear glass, amber glass, or plastic. In some embodiments, the vials may be in the range of about 0.1 to 500 mL in volume, preferably in the range of about 0.5 to 250 mL, more preferably in the range of about 1 to 100 mL, and most preferably in the range of about 10 to 50 mL. In some embodiments, the composition may exist in a 5 mL vial. In some embodiments, the 5 mL vial may be a single-dose formulation. In some embodiments, the 10 mL vial may be a multi-dose formulation. In some embodiments, the same vial may be used for multiple applications of the composition for up to about 10 days after initial use, preferably up to about 15 days, more preferably up to about 30 days, more preferably up to about 45 days, and most preferably up to about 60 days.

The polymeric materials which may be used include: polysulfone, polycarbonate, polypropylene, polyethylene (LDPE or HDPE), ethylene/propylene copolymers, polyolefins, acrylic-imide copolymers, polyester (e.g. PET, PEN and the like), Teflon, Nylon, acetal (Delrin), polymethylpentene, PVDC, ethylvinylacetate, AN-copolymer etc. In addition, crystal zenith (CZ) resin containers and similar resins can be used as rigid containers and syringes.

A ready-to-use pre-filled syringe comprising sterile and stable meloxicam emulsion according to the invention will be advantageous, as compared to the individual compositions. A pre-filled syringe fabricated from a polymer will not only be convenient for handling, storage and administration, but will also minimize mixing or dosing errors. The pre-filled syringe according to the invention may include single use auto injectors and reusable auto injectors.

The emulsion preparations as described herein may further comprise effective amounts of one or more other therapeutically active ingredient. Suitable other active ingredients used in some of the embodiments of present disclosure include, but are not limited to, Nonsteroidal anti-inflammatory drugs (NSAIDs), opioids, corticosteroids, anaesthetic agents or mixtures thereof.

The pharmaceutical compositions of the present disclosure can be used for the treatment of osteoarthritis, rheumatoid arthritis, and acute pain and provide a non-oral option for patients having moderate or severe pain. The disclosure thus encompasses a method of treatment comprising intravenously or intramuscularly administering meloxicam emulsion as described herein to a subject having moderate or severe pain.

EXAMPLES

The following examples are exemplary and not intended to be limiting. The above disclosure provides many different embodiments for implementing the features of the invention, and the following examples describe certain embodiments. It will be appreciated that other modifications and methods known to one of ordinary skill in the art can also be applied to the following experimental procedures, without departing from the scope of the invention.

Example 1

Pharmaceutical Compositions of Meloxicam

| Ingredients | Composition A mg/mL | Composition B mg/mL | Composition C mg/mL |
|---|---|---|---|
| Meloxicam | 1.7 | 1.7 | 1.7 |
| Egg lecithin | 144.4 | 144.4 | 144.4 |
| Ethanol | 27.8 | 27.8 | 27.8 |
| Sodium oleate | 5.6 | 5.6 | 5.6 |
| Soybean oil | 94.4 | 94.4 | 94.4 |
| Sucrose | 55.6 | — | — |
| Sodium chloride | — | 9 | — |
| Propylene glycol | — | — | 20 |
| Water for Injection | 670.5 | 717 | 701 |

Brief Manufacturing Process:
Oil Phase Preparation:
1. Ethanol, meloxicam and egg lecithin (Lipoid E 80) were added to a vessel.
2. The mixture was heated to about 60° C. and stirred for 15 minutes to form a solution.
3. Soybean oil was added to the mixture and stirring was continued at 60° C. for 15 minutes.

Aqueous Phase Preparation:
1. Required quantity of sucrose, sodium chloride, propylene glycol and sodium oleate were added to water for injection in an another vessel.
2. The contents were stirred for 30 minutes to obtain a clear solution.

Crude Emulsion Preparation:
3. The aqueous phase was added to the oil phase and the mixture was subjected to high speed homogenization (using Ultra Turrax IKA T 25) at a speed of 20,000 rpm for 1 min to produce the crude emulsion.

Micro Fluidization:
4. The crude emulsion was passed 8 times through ice cooled microfluidizer at a pressure of 18,000 psi.
5. The fine emulsion was filtered through 0.2-micron nylon syringe filter.
6. pH of the filtered fine emulsion was found to be in the range of 7.5 to 9.0.

Stability data was generated by subjecting composition A of example 1 to 12 months storage at 2-8° C. The stability data indicated that the globule size of the fine emulsion remained constant.

TABLE 1

| | | Tests | | |
|---|---|---|---|---|
| | | Globule size data | | |
| Stage | Description | D10 | D50 | D90 |
| Crude Emulsion (before micro fluidization) | Not Applicable | 2.523 μm | 6.365 μm | 12.258 μm |
| Fine Emulsion (Initial) | Opaque, off-white to amber colour liquid | 0.133 μm | 0.180 μm | 0.252 μm |
| Fine Emulsion (after 12 months storage at 2-8° C.) | Opaque, off-white to amber colour liquid | 0.075 μm | 0.111 μm | 0.168 μm |

While the invention has been described above with reference to specific embodiments thereof, it is apparent that many changes, modifications, and variations can be made without departing from the inventive concept disclosed herein, and such description is not intended as limitations on the scope thereof. Accordingly, it is intended to embrace all such changes, modifications, and variations that fall within the spirit and broad scope of the appended claims.

The invention claimed is:

1. A method of treating osteoarthritis, rheumatoid arthritis, and acute pain comprising parenterally administering to a human patient, a pharmaceutical formulation comprising a stable emulsion of meloxicam, wherein said emulsion comprises:
   meloxicam or a pharmaceutically acceptable salt thereof;
   a first emulsifier;
   an oil which is soybean oil;
   a second emulsifier which is ethanol;
   a pH modifier;
   an osmotic agent
   and water;
   wherein the meloxicam is dissolved in the ethanol and the soybean oil to form an oil phase;
   wherein the pH of the emulsion ranges from about 7.0 to 10;
   wherein said emulsion has an intensity-weighted mean droplet diameter less than about 300 nm.

2. The method of claim 1, wherein the emulsion comprises 5 wt/wt % to 25 wt/wt % of the first emulsifier.

3. The method of claim 1, wherein the first emulsifier is a phospholipid.

4. The method of claim 1, wherein the first emulsifier is egg lecithin.

5. The method of claim 1, wherein the emulsion comprises 5 wt/wt % to 15 wt/wt % of soybean oil.

6. The method of claim 1, wherein the pH modifier is sodium oleate.

7. The method of claim 1, wherein the emulsion comprises less than 10 wt/wt % of ethanol.

8. The method of claim 1, wherein the osmotic agent is sodium chloride or sucrose.

9. A method of treating osteoarthritis, rheumatoid arthritis, and acute pain comprising parenterally administering to a human patient, a pharmaceutical formulation comprising a stable emulsion of meloxicam,
   wherein said method comprises preparing the emulsion of meloxicam comprising the steps:
   (i) combining meloxicam, a first emulsifier, and a second emulsifier which is ethanol, with an oil which is soybean oil to generate an oil phase in which the meloxicam is dissolved;
   (ii) combining water, an osmotic agent and a pH modifier to generate an aqueous phase;
   (iii) homogenizing the oil phase with the aqueous phase to generate a coarse emulsion premix;
   (iv) homogenizing the coarse emulsion premix at a pressure between 10,000 and 30,000 psi using a microfluidizer to generate the pharmaceutical emulsion; and (v) sterilizing the pharmaceutical emulsion
wherein said emulsion has an intensity-weighted mean droplet diameter less than about 300 nm.

10. The method according to claim 9, wherein said step of homogenizing the coarse emulsion premix comprises 4 to 15 passes through the microfluidizer.

11. The method according to claim 9, wherein said step of sterilizing comprises passing the pharmaceutical emulsion through a filter having a pore size of about 0.2 micrometre.

12. A method of treating osteoarthritis, rheumatoid arthritis, and acute pain comprising parenterally administering to a human patient, a pharmaceutical formulation comprising a stable emulsion of meloxicam, wherein the emulsion comprises: meloxicam or a pharmaceutically acceptable salt thereof;
- a first emulsifier;
- an oil which is soybean oil;
- a second emulsifier which is ethanol;
- a pH modifier;
- an osmotic agent and water; wherein the meloxicam is dissolved in the ethanol and the soybean oil to form an oil phase;
- wherein the pH of the emulsion ranges from about 7.0 to 10,
- wherein said first emulsifier is phospholipid, egg lecithin or a mixture thereof, and said ethanol is present in the amount of 10% by weight;
- wherein said emulsion has an intensity-weighted mean droplet diameter less than about 300 nm.

* * * * *